United States Patent [19]

Fleming et al.

[11] 4,120,592
[45] Oct. 17, 1978

[54] MULTIPLEX OPTICAL ANALYZER APPARATUS

[75] Inventors: Sydney Winn Fleming, Wilmington, Del.; Gregory Paul Weeks, Waynesboro, Va.

[73] Assignee: E. I. Du Pont de Nemours and Company, Wilmington, Del.

[21] Appl. No.: 670,079

[22] Filed: Mar. 24, 1976

[51] Int. Cl.² .......................................... G01N 21/24
[52] U.S. Cl. .................................. 356/201; 250/343; 356/184; 356/188; 356/51
[58] Field of Search .................. 356/51, 88, 93–95, 356/97, 179, 180, 184, 186, 188, 189, 195, 201, 204, 205; 250/343

[56] References Cited

U.S. PATENT DOCUMENTS

| 2,678,581 | 5/1954 | Reisner | 356/205 |
| 3,459,951 | 8/1969 | Howarth et al. | 356/205 X |
| 3,917,406 | 11/1975 | Siegler, Jr. | 356/88 |

FOREIGN PATENT DOCUMENTS 796,661  6/1958  United Kingdom .................... 356/205

OTHER PUBLICATIONS

Negus, Instruments & Control Systems, vol. 37, Aug. 1964, pp. 87–96.

*Primary Examiner*—F. L. Evans

[57] ABSTRACT

Apparatus for enlarging the analytical capability of a photometric analyzer for segregating a first preselected analytical radiation wavelength band for passage through a first sample cell and segregating a second preselected analytical radiation wavelength band for passage through a second sample cell, after which emergent radiations from both sample cells are directed to a common radiation detector.

7 Claims, 9 Drawing Figures

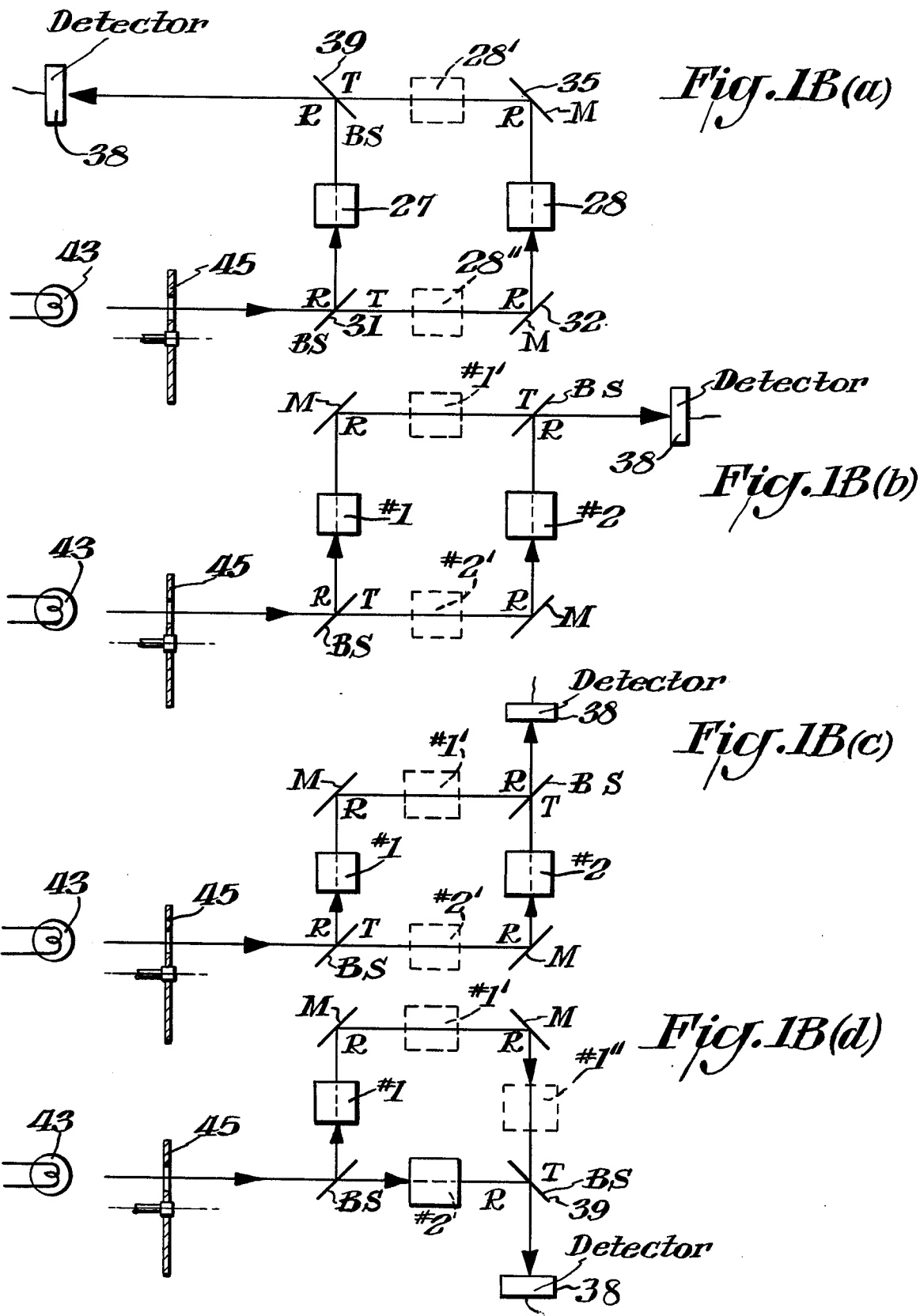

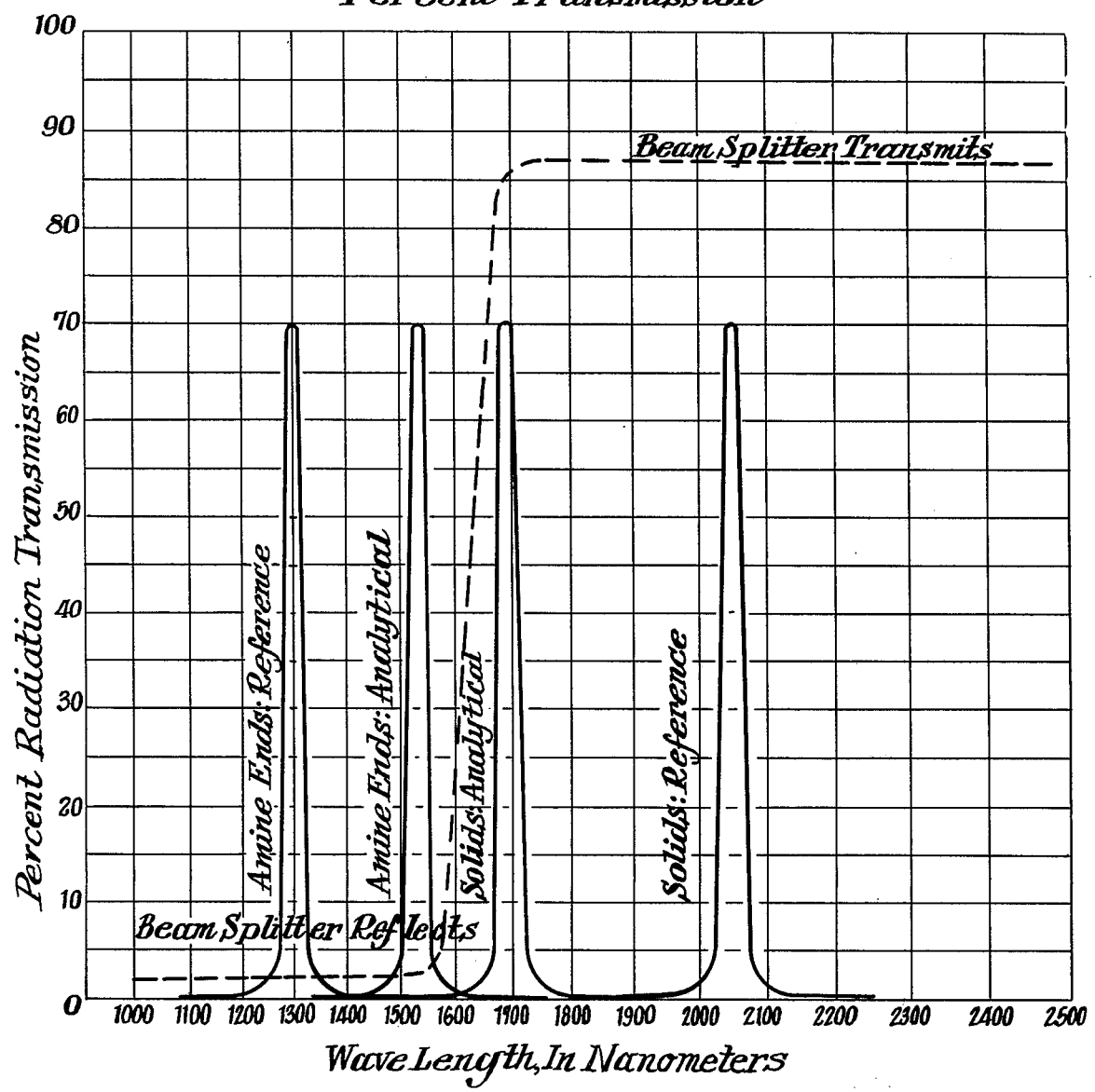

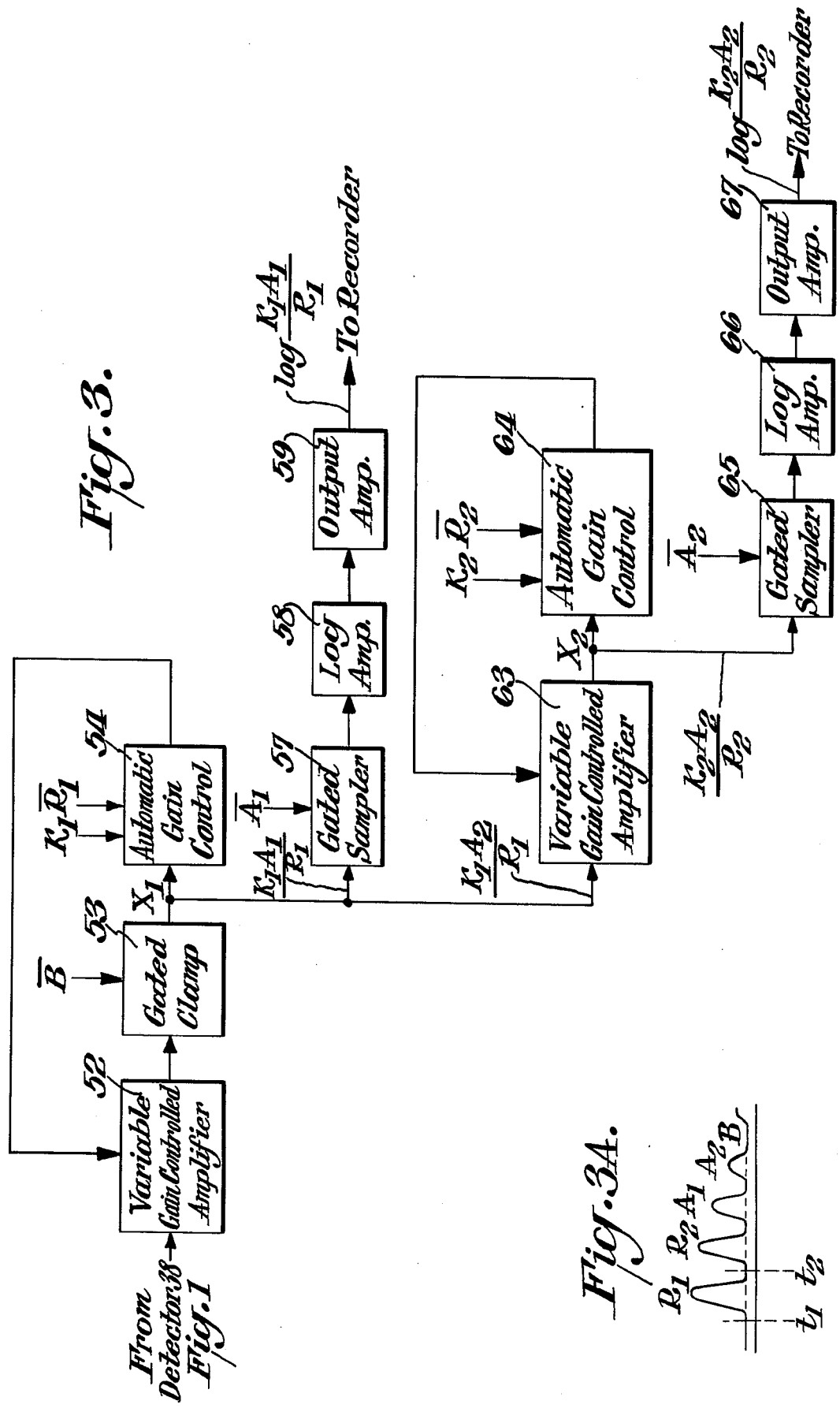

MULTIPLEX OPTICAL ANALYZER APPARATUS

RELATED PATENT APPLICATIONS

The invention of this Application is taught as utilizing a dual channel implicit ratio computer which is the subject of Application Ser. No. 670,080, cofiled herewith on Mar. 24, 1976, which Application is of common assignment herewith.

BRIEF SUMMARY OF THE INVENTION

Generally, this invention comprises apparatus for doubling, or even tripling, the analytical capabiltiy of a given photometric analyzer comprising means for splitting the radiation from a source into a first preselected reflected wavelength band passed through a first analytical cell and a second preselected transmitted wavelength band passed through a second analytical cell, and then passing the emergent radiations from the two cells to a common radiation detector.

DRAWINGS

The following schematic drawings depict a preferred embodiment of apparatus according to the invention in which.

FIGS. 1B($a$)–1B($d$) are schematic representations of four typical radiation routing arrangements which can be utilized according to this invention.

Figure 1A:
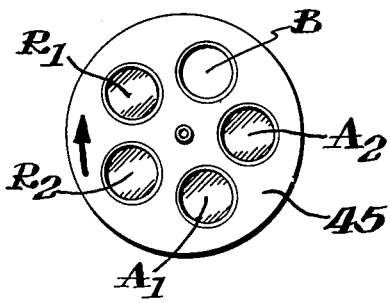
FIG. 1A is a front elevation view of a typical chopper wheel.
Figure 1:
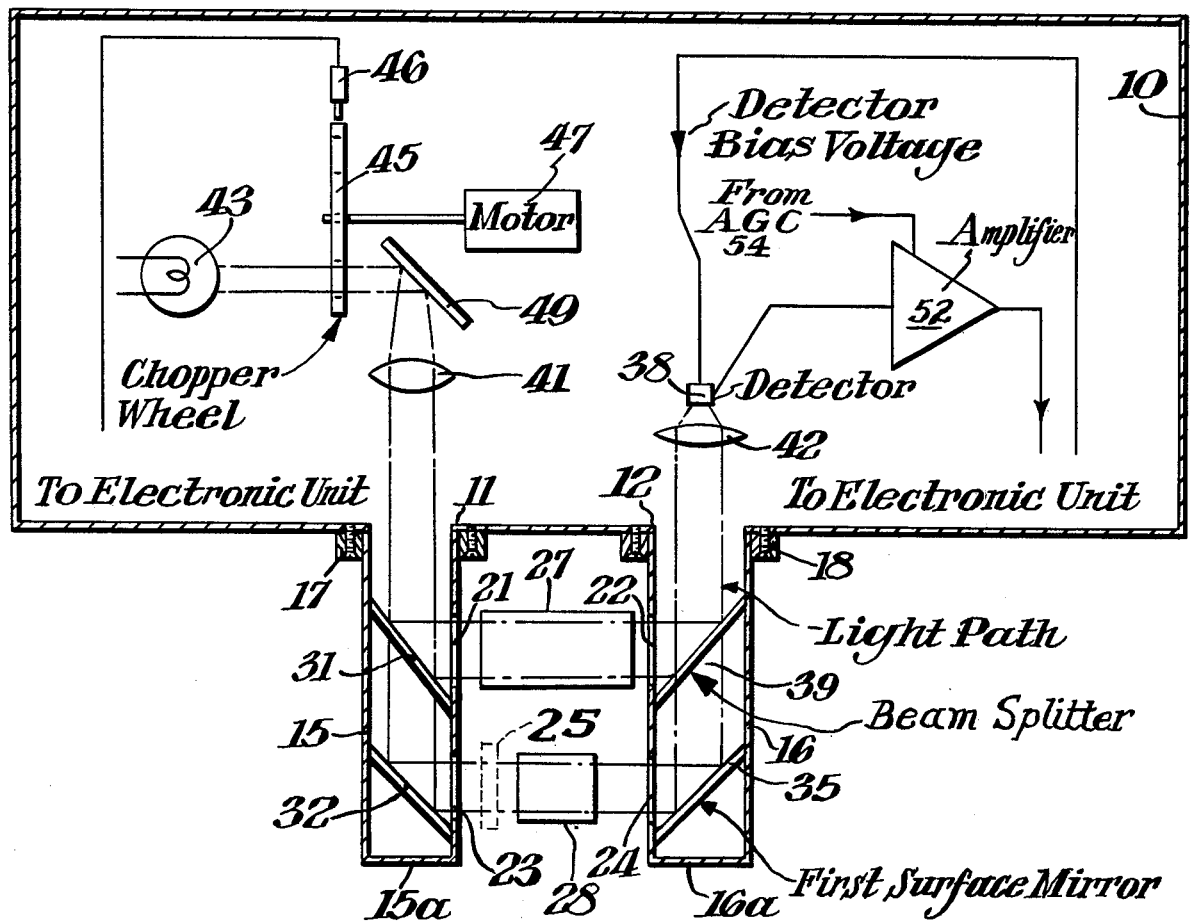
FIG. 1 is a plan sectional view of a complete optical portion of the analyzer.

FIG. 2 is a plot of percent radiation transmission, as ordinate, versus wavelength, as abscissa, for two components of separate process liquid samples, showing both analytical and reference radiations, FIG 3 is a block diagram of a typical electronic circuit for use with the apparatus of FIG. 1, and FIG. 3A is a schematic representaton of a typical electric analog signal pulse sequence which constitutes the input processed by the apparatus of this invention.

THE INVENTION

Referring to FIGS. 1 and 1A, it is convenient to attach the apparatus of this invention to a conventional photometric analyzer, such as that housed in enclosure cabinet 10 by simply providing radiation-passing apertures 11 and 12 in the enclosure wall and securing the radiation-transmitting conduits 15 and 16 thereto by flange-screw attachment denoted generally at 17 and 18. It is not absolutely essential that conduits be employed where infrared radiation analysis is conducted, as in the specific embodiment hereinafter described. However, such conduits are preferred, not only because they shield from outside radiation interference but also because the conduits can be given a reflective inside coating which conserves analytical radiation. In any case, conduits 15 and 16 constitute convenient mounts for beam splitters or other reflectors routing the radiation down preselected paths.

Conduits 15 and 16 can conveniently comprise coparallel lengths of aluminum tubing, approximately 1 inch inside diameter, closed with caps 15$a$ and 16$a$ at the outboard ends. Conduits 15 and 16 are provided with paired radial radiation-passing ports 21, 22 and 23, 24 disposed in aligned opposition.

Sequential control of radiation input and coordinated cyclical operation of the electronic circuit responsive to the radiation detector 38 is effected by chopper wheel 45 which is driven by motor 47 at a rate of, typically, 1800 rpm. Since there are four separate radiation wavelengths to be supplied via mirror 49 in the apparatus described, there are four separate optical interference filters reference $R_1$, reference $R_2$, analytical $A_1$, and analytical $A_2$, together with a blank filter B to provide a period of no radiation for background clamping during each full chopper wheel rotation. The five filters on chopper wheel 45 are spaced equiangularly of each other at angles of 72° apart. A conventional electromagnetic pickup 46 responsive to the circumferential rotational sweep of a magnetic material insert (not shown) in the periphery of chopper wheel 45 generates an electrical pulse signaling each rotation of chopper wheel 45.

In one preferred embodiment, sample cell 27 is mounted in lengthwise alignment within the radiation course defined by apertures 21 and 22, whereas sample cell 28 is mounted in lengthwise alignment within the radiation course 23, 24 by conventional mounting supports not detailed. Usually, the sample cells are provided with inlet and exit ports (not shown) for continuous circulation of a process liquor therethrough, where continuous monitoring of a manufacturing process is desired. However, cells 27 and 28 can, of course, be utilized for spot sample analysis when repetitive samples are taken at desired time intervals and analyzed individually. Yet another use is to employ sample cells 27 and 28 for completely separate individual analyses by circulation of one sample material to be analyzed through one cell, e.g., cell 27, while circulating the other sample material through the second cell, 28.

The segregation of preselected radiation wavelength bands is effected by a first beam splitter 31, which is preferably of the wavelength-selective type, such as a conventional dielectric filter, inclined towards sample cell 27 at an angle of 45° with respect to the axis of conduit 15. The reflected radiation from beam splitter 31 is chosen for selective absorption measurement of a given component of the sample contained within optically transparent sample cell 27, which can have a length proportioned to the particular analysis to be performed.

The transmitted radiation passed through beam splitter 31 is directed via full reflectance mirror 32, disposed at the same angle of 45° with respect to the axis of conduit 15 as beam splitter 31, through the aperture pair 23, 24 and also through interposed optically transparent sample cell 28, which also has a length proportioned to the particular analysis it is to perform.

The emergent radiations from sample cells 27 and 28 are conveniently directed along a common path axially of conduit 16 to common radiation detector 38. Thus, full reflectance mirror 35, inclined inwardly toward mirror 32 at an angle of 45°, directs the emergent radiation from analytical cell 28 for transmission through a second beam splitter 39, which can be identical with beam splitter 31, but inclinded inwardly at a 45° angle towards beam splitter 31. Also, the emergent radiation from sample cell 27 is directed coparallel the axis of conduit 16 by reflectance from the front face of beam splitter 39.

Convex lens 41 effects a partial collimation of the incoming radiation from radiation source 43, whereas convex lens 42 focuses the exiting radiation upon radiation detector 38.

Referring to FIGS. 1B($a$) to 1B($d$), showing four typical arrangements, there is considerable design flexibility in the choice of radiation routing paths according to this invention. Thus, FIG. 1B(a) represents the same arrangement as that of FIG. 1, the same mirror and beam splitter components being denoted by the same reference numerals. It will be clear that sample cell 28 can be equally well disposed at positions 28' or 28", except that symmetry of design makes the solid line position 28 preferred. Thus, it is convenient to mount the entire unitary assembly of conduits 15, 16 and the sample cells 27, 28 on tracks (not shown) so as to be movable towards and away from apertures 11 and 12 to permit convenient servicing of the several parts. Moreover, the design of FIG. 1B(a) is compact. The radiation routing modes in FIGS. 1B(a)–1B(d) inclusive are by reflection (R) and transmission (T), and the several optical components are identified as mirrors (M) and beam splitters (BS). In all instances solid line cells 27, 28 1 and 2 are, normally, preferred dispositions, whereas broken line cells 28', 28", 1', 1", and 2' are less preferred. However, each design may have merit in special circumstances.

As is known in the art, absorption type photometric analyzers, for measuring the concentration of a component in a sample, function most satisfactorily when the thickness of the sample is adjusted so that the light reaching the detector 38 approximates a value of 1/e times that for zero concentration, i.e., about 37%. As a practical matter, a value between 20 and 60% transmission in the analytical wavelength band is usually satisfactory.

Where two analyses are desired for components having widely different absorption characteristics, however, no single sample thickness will meet the above criteria for both analyses. It is therefore an object of this invention to provide apparatus whereby a single analyzer can be multiplexed to perform two or more analyses, each employing a sample of optimum thickness. In the case of fluid samples, this requires two or more sample cells of different path lengths along their respective optic axes.

Beam splitters 31 and 39 are commercially available optical devices which separate an incident beam of radiation into two parts, one part being transmitted through the beam splitter and the other part being reflected from its front face. A preferred configuration is that shown in FIG. 1 wherein the beam splitter is disposed at an angle of 45° to the incident optic axis, so that the reflected beam is directed at 90° to the incident beam, and the transmitted beam is an extension of the incident beam.

The beam splitter can be either a wavelength-selective type or a wavelength non-selective type. Any dielectric interference filter can be used as a wavelength-selective beam splitter, since wavelength transmission of the desired radiation wavelength is obtained by reflection of unwanted wavelengths. Thus, the reflected component contains wavelengths not transmitted, and vice versa. It will be understood, however, that transmission and reflection characteristics will be altered somewhat when the filter is employed at an angle other than that for which it was designed. Generally, for purposes of this invention, the preferred form of wavelength-selective beam splitter will embody a filter of the cut-off variety, so that all radiation wavelengths above or below a preselected wavelength will be transmitted, whereas the balance of the radiation is reflected.

Wavelength non-selective beam splitters can be manufactured with either a dielectric or metallic coating arranged so that all wavelengths within the region of interest are partially transmitted and partially reflected, making the two beams substantially identical as regards wavelength. The relative radiation intensities can be preselected by design so that any desired ratio of intensities is obtained.

A single beam splitter is employed in FIG. 1 to direct analytical radiation beams from both samples along a common axis to a common detector 38. In the case of wavelength-selective types, beams of different wavelengths separated at high efficiency by a dielectric interference beam splitter 31 can be directed at high efficiency by a substantially identical beam splitter 39 disposed so that the previously transmitted beam is transmitted in the reverse direction through the second beam splitter, and the previously reflected beam is again reflected from its surface, which is arranged at such an angle that the two beams follow coincident paths after passage through or reflection via the second beam splitter, thereby impinging on the common detector.

There may be cases where a ratio of intensities other than unity may be desirable, either to optimize performance of the analysis most handicapped by high background absorbance or other photometric parameter, or to reduce potential interference between channels. For example, if the two samples differ in thickness by a factor of 10 for the two analyses, the radiation passing through the thinner cell at the wavelength employed for analysis in the thicker cell would constitute "stray light". This would decrease measurement sensitivity and contribute to non-linearity of response. This effect can be minimized by dividing the radiation unequally between the two paths, so that the thicker cell receives substantially more radiation than the thinner cell. The limit to this approach depends on the minimum radiation intensity required to allow the optical system to function, which, as a practical matter might be 10–20% of the intensity in the stronger beam. An alternative approach is to employ equal division of intensities using non-selective beam splitters, but in addition using an auxiliary wavelength isolation means 25 in the beam passing through the thin cell. Such an auxiliary means can be an interference cut-off filter which passes radiation needed for analysis in the thin cell while blocking, or at least severely reducing, radiation of a wavelength needed for analysis in the thick cell. It will be understood that the transmitted beam will be still further attenuated upon routing by the second beam splitter. No basic reason exists for using two beam splitters of either identical or purposely different types; it is simply necessary to take the splitting and recombination ratios into account for both devices, so as to establish the needed intensities.

Referring now to FIG. 3, there is shown a preferred design of an electrical circuit for use in conjunction with the apparatus of FIGS. 1, 1A and 1B(a)–1B(d). This circuit is the subject of Application Ser. No. 670,080 supra, cofiled on the same date herewith, in the name of Edward S. Ida, a fellow employee of the common assignee, E. I. du Pont de Nemours and Company, and is therefore described only generally herein.

Thus, as viewed in FIG. 1A, there are generated five characteristic electrical signals representative of the several filtered radiations, and in the sequence of their respective inputs (refer FIG. 3A), as chopper wheel 45 rotates in a clockwise sense across the radiation path of source 43, FIG. 1, these signals being identified $R_{1+B}$, $R_2 + B$, $A_1 + B$, $A_2 + B$ and B (i.e., Background) as represented schematically in FIG. 3A.

In accordance with the principles of photometric analysis, it will be understood that a quantitative measure of the content of a given constituent in one sample cell, e.g., sample cell 27, is the logarithmic ratio of a constant, $K_1$, times $A_1/R_1$, whereas the content of another constituent in the other sample cell, i.e., sample cell 28, is the logarithmic ratio of a constant, $K_2$, times $A_2/R_2$, where $R_1$ and $R_2$ are reference values and $A_1$ and $A_2$ are the analytic signal values characterizing, respectively, the concentrations of the constituents to be measured.

In FIG. 3, the pulse signals from detector 38, FIG. 1, are first supplied to variable gain-controlled amplifier 52 having gain G and thence to gated clamp 53, which clamps the GB signal to zero and makes the pulse amlitudes equal to $GR_1$, $GR_2$, $GA_1$, $GA_2$ and zero, respectively. The output of clamp 53 is input to automatic gain control circuit 54, which functions as a gated integrator to force the integrated difference between a constant $K_1$ and the clamped signal $GR_1$ to zero. This is expressed mathematically as $$\left[ \int_{t_1}^{t_2} (GR_1 - K_1)dt \right]_{avg.} = 0,$$

where $t_1$ and $t_2$ are the time period limits of the $R_1$ pulse as indicated in FIG. 3A. Consequently, $K_1 = GR_1$ where G = the gain of amplifier 52, or $G = K_1/R_1$. The combined action of the gated integrator in control circuit 54 and the gated clamp 53 in the feedback configuration described produces output signals at point $X_1$ in the loop which have amplitudes in the sequence $K_1$, $K_1R_2/R_1$, $K_1A_1/R_1$, $K_1A_2/R_1$, zero and so forth in repetition of the cycle.

A separate sampling circuit is reserved for each logarithmic ratio to be analyzed, e.g., log $K_1A_1/R_1$, such that, when gated by the particular logic signal, e.g., $\overline{A_1}$, gated sampler 57 in series with logarithmic amplifier 58 and output amplifier 59 generates the desired signal, log $K_1A_1/R_1$, which is supplied to a conventional recorder, not shown, reporting the analysis of the first constituent, i.e., that in sample cell 27.

Similarly, as detector 38 generates the signals $R_2$ and $A_2$ in sequence, these are supplied through clamping circuit 53 to a separate variable gain-controlled amplifier 63 provided with an automatic gain control circuit 64. In a similar manner, the feedback delivered in this circuit generates $K_2A_2/R_2$ at point $X_2$ as a member of the pulse sequence $K_2R_1/R_2$, $K_2$, $K_2A_1/R_2$, $K_2A_2/R_2$ and zero, which, upon gating by the $A_2$ logic signal applied to gated sampler 65, produces an output voltage passed to logarithmic amplifier 66 and output amplifier 67, namely the desired log $K_2A_2/R_2$. This value can be read out on another conventional recorder, not shown, reporting the analysis of the second constituent, i.e., that in sample cell 28.

EXAMPLE

This invention has been utilized successfully to analyze simultaneously amine ends and bright polymer solids existing in spandex polymer solutions of the compositions described in U.S. Pat. No. 3,557,044, property of common assignee.

The apparatus of this invention was coupled to an infrared analyzer apparatus in the configuration shown in FIGS. 1 and 1B(a). The radiation time sequence selector consisted of a chopper wheel 45, rotating at 1800 rpm, constituting part of the analyzer itself, which was provided with four narrow band interference filters of bandwidth approximately 50 nm and peak transmission wavelengths of the following values (refer FIG. 2):

(1) 1300 nm Amine End Groups Reference
(2) 1535 nm Amine End Groups Analytical
(3) 1695 nm Polymer Solids Conc. Analytical
(4) 2050 nm Polymer Solids Conc. Reference An amine ends transmission cell having a length of 8 cm. was utilized as sample cell 27 (FIG. 1), whereas a solids transmission cell of 1 cm. length was used as sample cell 28. The process fluid was made to flow continuously through both cells in series in the order of sample cell 27 thence sample cell 28.

The process fluid consisted of an isocyanate-terminated polyether glycol dissolved in N,N-dimethyl acetamide chain-extended with diamine, as described in U.S. Pat. No. 3,557,044 supra.

Two identical wavelength-selective Infrared Industries, Inc. beam splitters were disposed in the optical arms as shown in FIG. 1, beam splitter 31 reflecting wavelengths below 1600 nm with 98% efficiency while transmitting wavelengths above 1600 nm with ~85% efficiency, with a "cut-off" transition region between 1600 and 1650 nm.

Thus, amine ends transmission cell 27 was disposed athwart the reflected radiation, whereas solids transmission cell 28 was disposed athwart the transmitted radiation from beam splitter 31.

The second beam splitter 39 brought the emergent radiation from the first sample cell 27 and the second sample cell 28 into coincidence and directed it to detector 38. An electronic system such as that detailed in FIG. 3 was employed to process the analytical signals, and both ends and solids concentration values were recorded continuously.

What is claimed is:

1. In an absorption type photometric analyzer having a radiation source, means for sequencing radiation wavelengths, radiation collimating means and a radiation detector operating in synchronization with the means for sequencing radiation wavelengths, a radiation routing apparatus receiving analytical radiation from said radiation collimating means comprising: means for splitting said analytical radiation into first and second beams of preselected wavelength bands and for reflecting said first beam of preselected wavelength band through a first sample cell disposed athwart said first beam of preselected wavelength band of radiation to form a first beam of emergent radiation, and for transmitting said second beam of preselected wavelength band through a second sample cell disposed athwart said second beam of preselected wavelength band of radiation to form a second beam of emergent radiation; and means for merging the first and second beams of emergent radiation along a coincident path to said detector.

2. The photometric analyzer as defined in claim 1, said means for splitting said analytical radiation into beams of first and second preselected wavelength bands and said means for merging said beams of emergent radiation along a coincident path being of the wavelength selective type.

3. The photometric analyzer as defined in claim 1, said means for splitting said analytical radiation into first and second preselected wavelength bands and said means for merging said emergent radiations along a coincident path being of the nonselective wavelength type, and wherein said first sample cell is thicker than said second sample cell, and wherein an auxiliary wavelength selective isolation means is interposed across the radiation path through said second sample cell to bar passage of radiation through said second sample cell of analytical and reference wavelengths routed to said first sample cell.

4. In an absorption type photometric analyzer having a radiation source, means for sequencing radiation wavelengths, radiation collimating means and a radiation detector operating in synchronization with the means for sequencing radiation wavelengths, a radiation routing apparatus receiving analytical radiation from said radiation collimating means comprising: means for splitting said analytical radiation into first and second beams of preselected wavelength bands and for reflecting said first beam of preselcted wavelength band through a first sample cell to form a first beam of emergent radiation; means for reflecting said second beam of preselected wavelength band through a second sample cell to form a second beam of emergent radiation; and means for merging the first and second beams of emergent radiation along a coincident path to said detector.

5. The photometric analyzer as defined in claim 4, said means for splitting said analytical radiation into beams of first and second preselected wavelength bands and said means for merging said beams of emergent radiation along a coincident path being of the wavelength selective type.

6. The photometric analyzer as defined in claim 4, said means for splitting said analytical radiation into first and second preselected wavelength bands and said means for merging said emergent radiations along a coincident path being of the nonselective wavelength type, and wherein said first sample cell is thicker than said second sample cell, and wherein an auxiliary wavelength selective isolation means is interposed across the radiation path through said second sample cell to bar passage of radiation through said second sample cell of analytical and reference wavelengths routed to said first sample cell.

7. In an absorption type photometric analyzer having a radiation source, means for sequencing radiation wavelengths, radiation collimating means and a radiation detector operating in synchronization with the means for sequencing radiation wavelengths, a radiation routing apparatus receiving analytical radiation from said radiation collimating means comprising: means for splitting said analytical radiation into first and second beams of preselected wavelength bands and for reflecting said first beam of preselected wavelength band through a first sample cell to form a first beam of emergent radiation; means for reflecting said second beam of preselected wavelength band though a second sample cell to form a second beam of emergent radiation; means for merging the first and second beams of emergent radiation along a coincident path to said detector, said first sample cell being thicker than said second sample cell; and an auxiliary wavelength selective isolation means interposed across the radiation path through said second sample cell to bar passage of radiation through said second sample cell of analytical and reference wavelengths routed to said first sample cell.

* * * * *